United States Patent

Muro et al.

[11] 3,954,776
[45] May 4, 1976

[54] 1-[METHYLATED PIPERIDINO(AND PYRROLIDIN-1-YL)]-3-(SUBSTITUTED PHENOXY)-2PROPANOLS

[75] Inventors: Tomio Muro; Sogo Fukuzawa, both of Nakatsu; Yasuaki Chihara, Fukuoka; Tohru Nakao, Fukuoka; Kiyoshi Ogawa, Fukuoka, all of Japan

[73] Assignee: Yoshitomi Pharmeceutical Industries, Ltd., Osaka, Japan

[22] Filed: Aug. 23, 1974

[21] Appl. No.: 499,948

[30] Foreign Application Priority Data

Aug. 23, 1973 Japan.............................. 48-94977
Aug. 23, 1973 Japan.............................. 48-94978

[52] U.S. Cl...................... 260/293.67; 260/293.68; 260/293.69; 260/293.73; 260/293.83; 260/296 R; 260/326.5 D; 260/326.5 S; 260/326.5 SM; 260/326.5 SF; 260/326.5 M; 424/263; 424/267; 424/274

[51] Int. Cl.²........................................ C07D 211/14

[58] Field of Search.................. 260/293.67, 293.68, 260/293.69, 296 R, 326.5 D, 326.5 SM

[56] References Cited
UNITED STATES PATENTS
3,723,476  3/1973  Nakanishi et al............. 260/293.68

*Primary Examiner*—Sherman D. Winters
*Attorney, Agent, or Firm*—Sughrue, Rothwell, Mion, Zinn & Macpeak

[57] ABSTRACT

1-[Methylated piperidino (and pyrrolidin-1-yl)]-3-(substituted phenoxy)-2-propanols of the formula:

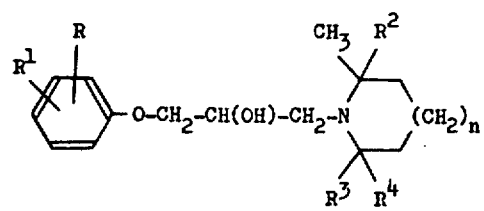

wherein R is a 2-thienylmethyl group, a 2-pyridylmethyl group, a 2-pyridyl group, a tetrahydrofurfuryloxy group, a furfuryloxy group, a 2-thienylmethoxy group, a 2-pyridyloxy group or a group of the formula $R^5—X—A—O—$ wherein $R^5$ is a lower alkyl group, X is $—O—$, $—S—$ or $—SO_2—$, and A is a lower alkylene group or a $—CH_2—C-C—CH_2—$ group, $R^1$ is a hydrogen atom, a lower alkyl group or a halogen atom, $R^2$, $R^3$ and $R^4$ are each a hydrogen atom or a methyl group, and n is zero or 1, and pharmaceutically acceptable acid addition and quarternary ammonium salts thereof are disclosed. They exhibit antiarrhythmic action, local anaesthetic action, analgesic action and gastric juice secretion inhibiting action.

16 Claims, No Drawings

1-[METHYLATED PIPERIDINO(AND PYRROLIDIN-1-YL)]-3-(SUBSTITUTED PHENOXY)-2-PROPANOLS

This invention relates to novel 1-[methylated piperidino (and pyrrolidin-1-yl)]-3-(substituted phenoxy)-2-propanols of the formula:

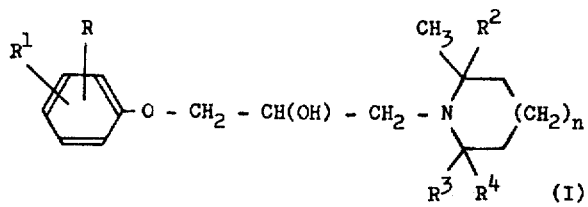

and pharmaceutically acceptable acid addition and quaternary ammonium salts thereof, pharmaceutical compositions containing the said compounds and the use thereof.

In the above formula (I), R is a 2-thienylmethyl group, a 2-pyridylmethyl group, a 2-pyridyl group, a tetrahydrofurfuryloxy group, a furfuryloxy group, a 2-thienylmethoxy group, a 2-pyridyloxy group or a group of the formula $R^5$—X—A—O- wherein $R^5$ is a lower alkyl group, X is —O—, —S— or —SO$_2$—, and A is a alkylene group or a -CH$_2$-C ≡ C-CH$_2$- group; $R^1$ is a hydrogen atom, a lower alkyl group or a halogen atom; $R^2$, $R^3$ and $R^4$ are each a hydrogen atom or a methyl group; and $n$ is zero or 1.

The lower alkyl group represented by $R^1$ and $R^5$ includes methyl, ethyl, propyl, isopropyl, butyl and isobutyl. The halogen atom represented by $R^1$ includes F, Cl and Br. The lower alkylene group represented by A includes methylene, ethylene, propylene, trimethylene and 2-methyltrimethylene.

Preferred classes of compounds are those wherein $n$ is 1.

Compounds close to the compounds of the invention in chemical structure are those of the formula:

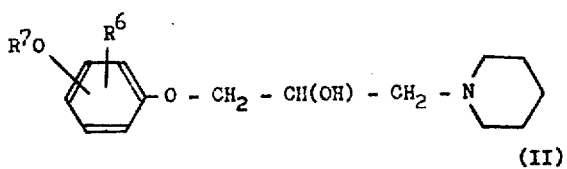

wherein $R^6$ is H, CH$_3$ or Cl, and $R^7$ is furylmethyl, thienylmethyl, tetrahydrofurylmethyl, pyridylmethyl or a group of the formula $R^8$ —X'—A— wherein $R^8$ is C$_{1-4}$ alkyl, C$_{1-4}$ alkenyl, phenyl or benzyl, X' is —O— or —S— and A is C$_{1-4}$ alkylene or —CH$_2$C ≡ CCH$_2$—, which are useful as β-adrenergic blocking agents (U.S. Pat. No. 3,723,476); and of the formula:

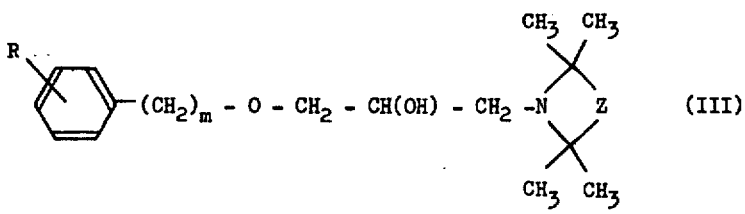

wherein Z is —CH$_2$—, —CH$_2$CH$_2$—, —CH=CH—, —CH$_2$CH$_2$CH$_2$—, —CH=CHCH$_2$—; R is H, CH$_3$, Cl or OCH$_3$; $m$ is zero, 1 or 2, which are useful as local anaesthetics (Arzneimittel-Forschung, 23, 275–278 (1973)).

Now the present invention provides novel compounds represented by formula (I) exhibiting antiarrhythmic action, local anaesthetic action, analgesic action and gastric juice secretion inhibiting action.

The compounds of formula (I) can be produced by reacting a compound of the formula:

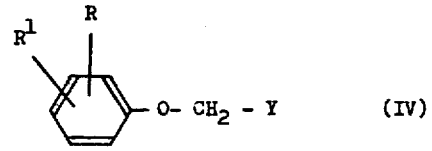

with a compound of the formula:

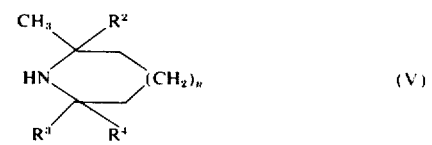

wherein R, $R^1$, $R^2$, $R^3$, $R^4$ and $n$ are as defined above, and Y is a group of the formula

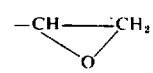

or —CH(OH) — CH$_2$— (halogen).

The reaction is usually carried out in an inert solvent such as methanol, ethanol, propanol, isopropanol, ether, dioxane, tetrahydrofuran, benzene, toluene, xylene, water, dimethylformamide, dimethyl sulfoxide or the like (preferably methanol or ethanol), at from room temperature to the boiling point of the solvent employed for from several hours to several days.

When a compound of formula (IV), wherein Y is —CH(OH)—CH$_2$—(halogen), is used as a starting material, the reaction may be carried out in the presence of an acid acceptor such as potassium carbonate, sodium carbonate, potassium hydroxide, sodium hydroxide, metallic sodium, sodium hydride, sodium amide, triethylamine or pyridine.

The compounds of formula (I) can also be produced by reacting a compound of the formula:

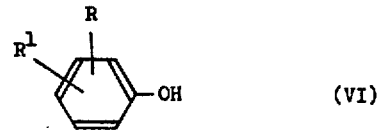

with a compound of the formula:

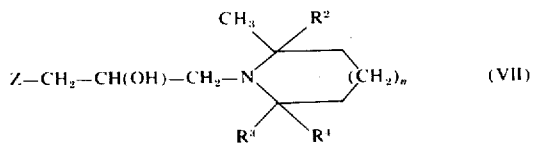

wherein R, R¹, R², R³, R⁴ and $n$ are as defined above, and Z is a halogen atom or alkyl- or aryl-sulfonyloxy such as methylsulfonyloxy or p-tolylsulfonyloxy, in an inert solvent such as mentioned above, in the presence of an acid acceptor such as mentioned above, at from room temperature to the boiling point of the solvent employed for from several hours to several days.

The compounds of formula (I) can be converted into acid addition salts with various inorganic and organic acids (e.g. hydrochloric, sulfuric, nitric, phosphoric, hydrobromic, oxalic, maleic, fumaric, malonic, o-(p-hydroxybenzoyl)benzoic acid, phenolphthalin), and also into quaternary ammonium salts with methyl chloride, methyl bromide, methyl iodide, butyl iodide, methyl hydrogensulfate or dimethyl sulfate.

The compounds of formula (I) are optically active compounds or racemic compounds. The racemic compounds, if desired, can be separated in a conventional manner into two enantiomers.

The compounds of formula (I) and salts thereof exhibit potent antiarrhythmic action, local anaesthetic action, analgesic action and gastric juice secretion inhibiting action, and are useful as drugs for the treatment and/or prevention of ventricular and atrial arrhythmias, arrhythmia during anaesthesia, post-opertive pain, gastric spasms, gastro-enteric ulcers, and the like, and also as anaesthetics, in the form of a pharmaceutical preparation with a suitable and conventional pharmaceutically acceptable carrier, without adversely affecting the patients.

The pharmaceutical preparations can take any conventional form such as tablets, capsules, granules, powders, injectable solutions, etc.

The dose of compound (I) or a salt thereof for human adults usually ranges from 15 to 60 mg per day for oral administration, and from 0.5 to 1 ml per time for intravenous administration, in single or multiple dose, but it may vary depending upon the age, body weight, and/or severity of the conditions to be treated as well as the response to the medication.

The present invention will be better understood from the following examples, but they are not to be construed as limiting the present invention.

EXAMPLE 1

1-(2,6-Dimethylpiperidino)-3-[2-(2-methoxyethoxy)-phenoxy]-2-propanol a. A mixture of 4.5 g of 1,2-epoxy-3-[2-(2-methoxyethoxy)phenoxy]-propane, 2.4 g of 2,6-dimethylpiperidine, 30 ml of methanol and 1 drop of water is refluxed for 8 hours. The methanol is then removed, and the residue is cooled. The precipitated colorless crystals are collected by filtration, and washed with petroleum benzine to give 5.2 g of 1-(2,6-dimethylpiperidino)-3-[2-(2-methoxyethoxy)phenoxy]-2-propanol, melting at 92°–94°C.

An ethereal solution containing this product (5.0 g) is added to a solution of 1.75 g of fumaric acid in a mixture of acetone and methanol (2 : 1, 30 ml), and the mixture is ice-cooled for 24 hours. The precipitated colorless crystals are collected by filtration, and recrystallized from a mixture of acetone and isopropyl ether to give 5.0 g of 1-(2,6-dimethylpiperidino)-3-[2-(2-methoxyethoxy) phenoxy]-2-propanol acid-fumarate, melting at 156°–157°C.

b. A mixture of 5.2 g of 1-chloro-3-[2-(2-methoxyethoxy)phenoxy]-2-propanol, 4.6 g of 2,6-dimethylpiperidine and 50 ml of ethanol is refluxed for 16 hours. The ethanol is removed, and ether is added to the residue. The insoluble matter is filtered off, and the filtrate is extracted with two 80 ml portions of 10% hydrochloric acid. The aqueous layer is made alkaline with sodium hydroxide, and the separated oil is extracted twice with ether. The ether layer is dried over anhydrous potassium carbonate, and the ether is removed to give 5.0 g of 1-(2,6-dimethylpiperidino)-3-[2-(2-methoxyethoxy)phenoxy]-2-propanol, melting at 92°–94°C.

c. 4.5 g of 1-chloro-3-(2,6-dimethylpiperidino)-2-propanol is added to a mixture of 3.4 g of 2-(2-methoxyethoxy)phenol, 2.8 g of anhydrous potassium carbonate and 70 ml of acetone, and the resulting mixture is refluxed with stirring for 20 hours. The insoluble matter is then filtered off, and the filtrate is concentrated under reduced pressure. To the residue is added ether, and the ethereal solution is extracted with two 80 ml portions of 10% hydrochloric acid. The aqueous layer is made alkaline with sodium hyroxide, and the separated oil is extracted twice with ether. The ether layer is dried over anhydrous potassium carbonate, and the ether is removed to give 4.6 g of 1-(2,6-dimethylpiperidino)-3-[2-(2-methoxyethoxy)phenoxy]-2-propanol, melting at 92°–94°C.

EXAMPLE 2

1-(2,6-Dimethylpiperidino)-3-[2-(2-thienylmethyl)-phenoxy]-2-propanol a. A solution of 2.5 g of 1,2-epoxy-3-[2-(2-thienylmethyl)phenoxy]-propane, 1.2 g of 2,6-dimethylpiperidine and 30 ml of ethanol is refluxed for 7 hours. The ethanol is then removed, and the residue is dissolved in ethyl acetate. The ethyl acetate solution is washed with water, dried over anhydrous magnesium sulfate, and the solvent is removed. The residue is purified by column chromatography using 70–325 mesh silica gel and a mixture of chloroform and methanol (100 : 2) as the eluent. The eluate fractions containing the objective product are combined and concentrated. The residue is dissolved in chloroform, and dried hydrogen chloride is introduced to the solution. The chloroform is removed to give 2.0 g of colorless crystals, which are recrystallized from a mixture of isopropanol and ethyl acetate to give 1.7 g of 1-(2,6-dimethylpiperidino)-3-[2-( 2-thienylmethyl)phenoxy]-propanol hydrochloride as colorless crystals, melting at 152°–153°C.

b. A solution of 2.8 g of 1-chloro-3[2-(2-thienylmethyl)phenoxy]-2-propanol, 2.3 g of 2,6-dimethylpiperidine in 30 ml of ethanol is refluxed for 15 hours. The ethanol is then removed, and the residue is dissolved in ether. The insoluble matter is filtered off, and the filtrated is extracted with two 50 ml portions of 10% hydrochloric acid. The aqueous layer is made alkaline with sodium hydroxide, and separated oil is extracted with ether. The ether layer is dried over anhydrous potassium carbonate, and the solvent is removed. The residue (crude product) is purified by column chromatography and converted into the hydrochloride in the same manner as in above method (a) to give 2.1 g of 1-(2,6-dimethylpiperidino)-3-[2-(2-thienylmethyl)-phenoxy]-2-propanol hydrochloride as colorless crystals, melting at 152°–153°C.

c. A mixture of 1.9 g of 2-(2-thienylmethyl)phenol, 2.3 g of 1-chloro-3-(2,6-dimethylpiperidino)-2-propanol, 1.4 g of anhydrous potassium carbonate, 30 ml of acetone and 20 ml of dimethylformamide is refluxed with stirring for 20 hours. The insoluble matter is then filtered off, and the filtrate is concentrated. To the residue is added ether, and the ethereal solution is extracted with two 50 ml portions of 10% hydrochloric acid. The aqueous layer is made alkaline with sodium hydroxide, and the separated oil is extracted twice with ether. The ether layer is dried over anhydrous potassium carbonate, and the solvent is removed. The residue is purified by column chromatography and converted into the hydrochloride in the same manner as in above method (a) to give 1.5 g of 1-(2,6-dimethyl-piperidino)-3-[2-(2-thienylmethyl)phenoxy]-2-propanol hydrochloride, melting at 152°–153°C.

EXAMPLE 3

1-(2,2,6,6-Tetramethylpiperidino)-3-[3-(2-pyridylmethyl)phenoxy]-2-propanol 19 g of epichlorohydrin is added to a mixture of 18.5 g of 3-(2-pyridylmethyl)phenol, 4.2 g of sodium hydroxide and 200 ml of methanol, and the resulting mixture is stirred at about 50°C for 3 hours. The methanol is then removed, water is added to the residue, and the aqueous solution is extracted with 200 ml of benzene. The benzene layer is washed with 5% sodium hydroxide and with water, and dried over anhydrous magnesium sulfate. The benzene is removed to give 15.0 g of 1,2-epoxy-3-[3-(2-pyridylmethyl)-phenoxy]-propane as oil.

8.9 g of 2,2,6,6-tetramethylpiperidine is added to a solution of 15.0 g of 1,2-epoxy- 3-[3-(2-pyridylmethyl)phenoxy]propane in 45 ml of n-amyl alcohol, and the resulting mixture is heated on a water bath for 2 hours. The solvent is then removed, 200 ml of benzene is added to the residue, and the insoluble matter is filtered off with activated charcoal. The filtrate is washed with water, and extracted with two 100 ml portions of 5% hydrochloric acid. The aqueous layer is made alkaline with sodium hydroxide, and the separated oil is extracted with benzene. The benzene layer is washed with water, dried over anhydrous potassium carbonate, and the solvent is removed. The residual oil is purified by distillation to give 4.5 g of 1-(2,2,6,6-tetramethylpiperidino)-3-[3-(2-pyridylmethyl)phenoxy]-2-propanol, boiling at 230°–235°C/0.15 mmHg.

A solution of 4.5 g of this product in 15 ml of acetone is added to a suspension of 1.37 g of fumaric acid in 15 ml of acetone, and 20 ml of isopropyl ether is further added. The mixture is allowed to stand. The precipitated colorless crystals are collected by filtration, and recrystallized from a mixture of methanol and isopropyl ether to give 2.3 g of 1-(2,2,6,6-tetramethyl-piperidino)-3-[3-(2-pyridylmethyl)phenoxy]-2-propanol fumarate hemihydrate, melting at 160°–162°C.

Using the procedure set forth in the above examples, but substituting equivalent amounts of the appropriate starting materials, the following compounds are also produced:

1. 1-(2-methylpiperidino)-3-[2-(tetrahydrofurfuryloxy)phenoxy]-2-propanol, $n_D^{20}$ 1.5290; its hydrochloride, melting at 115°–125°C;
2. 1-(2-methylpiperidino)-3-[2-(furfuryloxy)phenoxy]-2-propanol fumarate, melting at 129°–131°C;
3. 1-(2-methylpiperidino)-3-[2-(2-methylthioethoxy)phenoxy]-2-propanol hydrochloride, melting at 99°–101°C;
4. Almost equimolar mixture of 1-(2-methylpiperidino)-3-[4-methyl-2-(2-methoxyethoxy)-phenoxy]-2-propanol acid-furmarate and 1-(2-methylpiperidino)-3-[5-methyl-2-(2-methoxyethoxy)phenoxy]-2-propanol acid-fumarate, melting at 113°–117°C;
5. 1-(2-methylpiperidino)-3-[2-(2-thienylmethyl)-phenoxy]-2-propanol hydrochloride, melting at 131°–135°C;
6. 1-(2-methylpiperidino)-3-[4-(2-thienylmethyl)-phenoxy]-2-propanol hydrochloride, melting at 133°–134°C;
7. 1-(2,6-dimethylpiperidino)-3-[2-(2-methylthioethoxy)phenoxy]-2-propanol acid-maleate, melting at 111°–113°C; its hydrochloride, melting at 159°–160°C;
8. 1-(2,6-dimethylpiperidino)-3-[2-(tetrahydrofurfuryloxy)phenoxy]-2-propanol, melting at 80°–85°C; its hydrochloride, melting at 73°–78°C;
9. 1-(2,6-dimethylpiperidino)-3-[2-(2-thienylmethoxy)phenoxy]-2-propanol fumarate, melting at 145°–146°C;
10. 1-(2,6-dimethylpiperidino)-3-[2-(2-methylsulfonylethoxy)phenoxy]-2-propanol fumarate (monohydrate), melting at 108°–109°C;
11. 1-(2,6-dimethylpiperidino)-3-[2-(methoxymethoxy)phenoxy]-2-propanol, boiling at 185°–190°C/0.1 mmHg, melting at 59°–62°C;
12. Almost equimolar mixture of 1-(2,6-dimethylpiperidino)-3-[4-chloro-2-(2-methoxyethoxy)-phenoxy]-2-propanol and 1-(2,6-dimethyl-piperidino)-3-[5-chloro-2-(2-methoxyethoxy)-phenoxy]-2-propanol, melting at 70°–78°C;
13. Almost equimolar mixture of 1-(2,6-dimethylpiperidino)-3-[4-methyl-2-(2-methoxyethoxy)-phenoxy]-2-propanol acid-fumarate and 1-(2,6-dimethylpiperidino)-3-[5-methyl-2-(2-methoxyethoxy)phenoxy]-2-propanol acid-fumarate, melting at 129°–133°C;
14. 1-(2,2,6,6-tetramethylpiperidino)-3-[2-(2-methoxyethoxy)phenoxy]-2-propanol acid-fumarate, melting at 150°–152°C;
15. 1-(2,2,6,6-tetramethylpiperidino)-b 3-[2-(2-methylthioethoxy)phenoxy]-2-propanol hydrochloride, melting at 164°–167°C;
16. 1-(2,2,6,6-tetramethylpiperidino)-3-[2-(tetrahydrofurfuryloxy)phenoxy]-2-propanol, fumarate, melting at 140°–142.5°C;

17. 1-(2,2,6,6-tetramethylpiperidino)-3-[2-(furfuryloxy)phenoxy]-2-propanol fumarate, melting at 170°–172°C;
18. 1-(2,2,6,6-tetramethylpiperidino)-3-[2-(2-thienylmethoxy)phenoxy]-2-propanol acid-fumarate (1.5 hydrate), melting at 110°–120°C (decomposition);
19. 1-(2,2,6,6-tetramethylpiperidino)-3-[2-(2-pyridyloxy)phenoxy]-2-propanol fumarate, melting at 181°–182°C;
20. 1-(2,2,6,6-tetramethylpiperidino)-3-[2-(1-methyl-2-methoxyethoxy)phenoxy]-2-propanol fumarate, melting at 160°–163°C;
21. 1-(2,2,6,6-tetramethylpiperidino)-3-[2-(4-methoxy-2-butynyloxy)phenoxy]-2-propanol fumarate (monohydrate), melting at 148°–151°C;
22. Almost equimolar mixture of 1-(2,2,6,6-tetramethylpiperidino)-3-[4-methyl-2-(2-methoxyethoxy)phenoxy]-2-propanol acid-fumarate and 1-(2,2,6,6-tetramethylpiperidino)-3-[5-methyl-2-(2-methoxyethoxy)phenoxy]-2-propanol acid-fumarate, melting at 108°–111°C;
23. 1-(2,2,6,6-tetramethylpiperidino)-3-[2-(2-pyridylmethyl)phenoxy]-2-propanol 3/2 fumarate, melting at 114°–116°C;
24. 1-(2,2,6,6-tetramethylpiperidino)-3-[2-(2-thienylmethyl)phenoxy]-2-propanol hydrochloride, melting at 161°–162°C;
25. 1-(2,2,6,6-tetramethylpiperidino)-3-[4-(2-pyridyl)phenoxy]-2-propanol dihydrochloride, melting at 234°–235°C;
26. 1-(2,2,5,5-tetramethylpyrrolidin-1-yl)-3-[2-(2-methoxyethoxy)phenoxy]-2-propanol hydrochloride, melting at 126°–127°C;
27. 1-(2,2,5,5-tetramethylpyrrolidin-1-yl)-3-[2-(furfuryloxy)phenoxy]-2-propanol fumarate, melting at 138°–141.5°C;
28. Almost equimolar mixture of 1-(2,2,5,5-tetramethylpyrrolidin-1-yl)-3-[2-methyl-4-(2-methoxyethoxy)phenoxy]-2-propanol acid-fumarate and 1-(2,2,5,5-tetramethylpyrrolidin-1-yl)-3-[3-methyl-4-(2-methoxyethoxy)phenoxy]-2-propanol acid-fumarate, melting at 87°–91°C;
29. 1-(2,2,5,5-tetramethylpyrrolidin-1-yl)-3-[2-(2-thienylmethyl)phenoxy]-2-propanol acid-fumarate, melting a 119°–120°C;
30. 1-(2,6-dimethylpiperidino)-3-[4-(2-tetrahydrofurfuryloxy)phenoxy]-2-propanol.

PHARMACOLOGICAL TESTS

Methods

1. Antiarrhythmic action on functional refractory period

The test was performed essentially by the method described by G. Zetler et al in "Naunyn-Schmiedebergs Archiv für Pharmakologie", vol. 271, 335–345 (1971), using isolated guinea pig atria.

2. Infiltration anaesthetic action

The test was performed essentially by the method described by E. Bülbring et al in "Journal of Pharmacology and Experimental Therapeutics", vol. 85, 78–84 (1945), using guinea pig (male, about 400 g).

3. Surface anaesthetic action

The test was performed essentially by the method described by M.R.A. Chance et al in "Journal of Pharmacology and Experimental Therapeutics", vol. 82, 203–210 (1944), using guinea pig (male, about 400 g).

Results

1. Antiarrhythmic action on functional refractory period

| Test Compound | $EC_{50}$ (g/ml) |
|---|---|
| A | $2.4 \times 10^{-5}$ |
| B | $1.7 \times 10^{-5}$ |
| C | $1.3 \times 10^{-5}$ |
| D | $1.5 \times 10^{-5}$ |
| E | $2.2 \times 10^{-5}$ |
| F | $1.2 \times 10^{-5}$ |
| G | $1.8 \times 10^{-5}$ |
| Lotucaine | no effect |

2. Infiltration anaesthetic action

| Test Compound | Efficiency Rate (procaine = 1) |
|---|---|
| H | 51.7 |
| I | 98.7 |
| J | 35.6 |
| K | 167.5 |
| Lotucaine | 11.3 |

3. Surface anaesthetic action

| Test Compound | Efficiency Rate (procaine = 1) |
|---|---|
| B | 26.7 |
| C | 30.0 |
| D | 27.2 |
| G | 23.6 |
| I | 27.1 |
| L | 23.9 |
| Lotucaine | 11.1 |

Test Compound

A: 1-(2,2,6,6-tetramethylpiperidino)-3-[2-(2-methoxyethoxy)phenoxy]-2-propanol acid-fumarate B: 1-(2,2,6,6-tetramethylpiperidino)-3-[2-(tetrahydrofurfuryloxy)phenoxy]-2-propanol fumarate C: 1-(2,2,5,5-tetramethylpyrrolidin-1-yl)-3-[2-(furfuryloxy)phenoxy]-2-propanol fumarate D: 1-(2,2,6,6-tetramethylpiperidino)-3-[-2-(2-methylthioethoxy)phenoxy]-2-propanol hydrochloride E: 1-(2,2,6,6-tetramethylpiperidino)-3-[2-(2-pyridylmethyl)phenoxy]-2-propanol 3/2 fumarate F: 1-(2,2,6,6-tetramethylpiperidino)-3-[2-(2-pyridyloxy)phenoy]-2-propanol fumarate G: 1-(2,6-dimethylpiperidino)-3-[2-(2-thienylmethoxy)phenoxy]-2-propanol fumarate H: 1-(2,2,6,6-tetramethylpiperidino)-3-[2-(furfuryloxy)phenoxy]-2-propanol fumarate I: 1-(2,6-dimethylpiperidino)-3-[2-(2-thienylmethyl)phenoxy]-2-propanol hydrochloride J: 1-(2,2,6,6-tetramethylpiperidino)-3-[2-(2-thienylmethyl)phenoxy]-2-propanol hydrochloride K: 1-(2-methylpiperidino)-3-[2-(2-thienylmethyl)phenoxy]-2-propanol hydrochloride L: 1-(2-methylpiperidino)-3-[4-(2-thienylmethyl)phenoxy]-2-propanol hydrochloride Lotucaine: 1-(2,2,5,5-tetramethylpyrrolidin-1-yl)-3-(o-tolyloxy)-2-propanol hydrochloride (the compound of Arzneimittel-Forschung, 23, 275–278 (1973)).

FORMULATION EXAMPLES

The following is an example of formulations when a compound of the invention is administered for pharmaceutical purposes:

a. 5 m tablets are prepared from the following compositions:

| | |
|---|---|
| Compound (I) or a salt thereof | 5 mg |
| Lactose | 65 |
| Corn Starch | 15 |
| Crystalline Cellulose | 10 |
| Methyl Cellulose | 1 |
| Talc | 3 |
| Magnesium Stearate | 1 |
| | 100 mg | b. 0.5% injectable solutions are prepared from the following compositions:

| | |
|---|---|
| Compound (I) or a salt thereof | 5 mg |
| Sodium Chloride | 9 mg |
| Water for Injection | a sufficient quantity to make 1 ml |

Although the present invention has been adequately discussed in the foregoing specification and examples included therein, one readily recognizes that various changes and modifications may be made without departing from the spirit and scope thereof.

What is claimed is:

1. A compound of the formula:

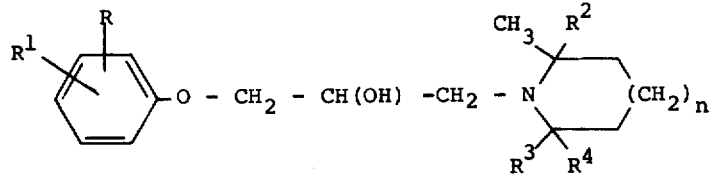

wherein R is a 2-thienylmethyl group, a 2-pyridylmethyl group, a 2-pyridyl group, a tetrahydrofurfuryloxy group, a furfuryloxy group or a 2-pyridyloxy group; $R^1$ is a hydrogen atom, a lower alkyl group or a halogen atom; $R^2$, $R^3$ and $R^4$ are each a hydrogen atom or a methyl group; and n is zero or 1; and pharmaceutically acceptable acid addition and quaternary ammonium salts thereof.

2. The compound of claim 1 wherein R is a 2-thienylmethyl group and $R^1$ is a hydrogen atom.

3. The compound of claim 1 wherein R is a 2-pyridylmethyl group and $R^1$ is a hydrogen atom.

4. The compound of claim 1 wherein R is a 2-pyridyl group and $R^1$ is a hydrogen atom.

5. The compound of claim 1 wherein R is a tetrahydrofurfuryloxy group and $R^1$ is a hydrogen atom.

6. The compound of claim 1 wherein R is a furfuryloxy group and $R^1$ is a hydrogen atom.

7. The compound of claim 1 wherein R is a 2-pyridyloxy group and $R^1$ is a hydrogen atom.

8. The compound of claim 1; 1-(2,2,6,6-tetramethylpiperidino)-3-[2-(tetrahydrofurfuryloxy)phenoxy]-2-propanol.

9. The compound of claim 1: 1-(2,2,5,5-tetramethylpyrrolidin-1-yl)-3-[2-(furfuryloxy)phenoxy]-2-propanol 10. The compound of claim 1: 1-(2,2,6,6-tetramethylpiperidino)-3-[2-(2-pyridylmethyl)phenoxy]-2-propanol 11. The compound of claim 1: 1-(2,2,6,6-tetramethylpiperidino)-3-[2-(2-pyridyloxy)phenoxy]-2-propanol 12. The compound of claim 1: 1-(2,2,6,6-tetramethylpiperidino)-3-[2-(furfuryloxy)phenoxy]-2-propanol 13. The compound of claim 1: 1-(2,6-dimethylpiperidino)-3-[2-(2-thienylmethyl)phenoxy]-2-propanol 14. The compound of claim 1: 1-(2,2,6,6-tetramethylpiperidino)-3-[2-(2-thienylmethyl)phenoxy]-2-propanol 15. The compound of claim 1: 1-(2-methylpiperidino)-3-[2-(2-thienylmethyl)phenoxy]-2-propanol 16. The compound of claim 1; 1-(2-methylpiperidino)-3-[4-(2-thienylmethyl)phenoxy]-2-propanol

* * * * *